United States Patent
Magnin

(10) Patent No.: US 7,810,503 B2
(45) Date of Patent: Oct. 12, 2010

(54) MANDIBULAR ADVANCEMENT SPLINT

(76) Inventor: Georges Magnin, Cret 37, La Sagne (CH) CH-2314

( * ) Notice: Subject to any disclaimer, the term of this patent is extended or adjusted under 35 U.S.C. 154(b) by 0 days.

(21) Appl. No.: 12/172,111

(22) Filed: Jul. 11, 2008

(65) Prior Publication Data
US 2009/0014013 A1    Jan. 15, 2009

Related U.S. Application Data

(60) Division of application No. 11/562,344, filed on Nov. 21, 2006, now abandoned, which is a continuation of application No. PCT/EP2005/052431, filed on May 27, 2005.

(30) Foreign Application Priority Data
Apr. 6, 2004    (EP)    ................ 2004-102543

(51) Int. Cl.
A61F 5/56    (2006.01)
A61C 3/00    (2006.01)

(52) U.S. Cl. .......................... 128/848; 433/6

(58) Field of Classification Search ......... 128/861–862, 128/859, 857, 846; 433/6, 19
See application file for complete search history.

(56) References Cited

U.S. PATENT DOCUMENTS

| | | | | |
|---|---|---|---|---|
| 5,683,244 A | * | 11/1997 | Truax | .............................. 433/6 |
| 5,829,441 A | | 11/1998 | Kidd et al. | |
| 5,947,724 A | * | 9/1999 | Frantz et al. | .................. 433/19 |
| 6,012,920 A | * | 1/2000 | Woo | .............................. 433/19 |
| 6,109,265 A | * | 8/2000 | Frantz et al. | .................. 128/848 |
| 6,170,485 B1 | | 1/2001 | Orrico | |
| 6,450,167 B1 | | 9/2002 | David et al. | |
| 6,526,982 B1 | | 3/2003 | Strong et al. | |
| 6,983,752 B2 | * | 1/2006 | Garabadian | .................. 128/848 |
| 7,077,646 B2 | * | 7/2006 | Hilliard | .......................... 433/6 |
| 2002/0000230 A1 | | 1/2002 | Gaskell | |
| 2007/0209666 A1 | * | 9/2007 | Halstrom et al. | ............. 128/859 |

FOREIGN PATENT DOCUMENTS

| | | |
|---|---|---|
| DE | 38 16 769 A1 | 8/1989 |
| DE | 19844628 A1 | 4/2000 |
| DE | 100 65 208 A1 | 7/2002 |
| DE | 102 16 242 C | 4/2003 |
| EP | 0845962 | 6/1998 |
| EP | 1 312 319 A3 | 5/2003 |
| WO | WO-01/80764 A1 | 11/2001 |

* cited by examiner

*Primary Examiner*—Patricia Bianco
*Assistant Examiner*—Tarla R Patel
(74) *Attorney, Agent, or Firm*—Blank Rome LLP

(57) ABSTRACT

Mandibular advancement splint against snoring and sleep apnea. The splint is made of two thermoformable trays (1, 2) designed to envelop the upper and lower arch. In order to be able to adapt to individual variations in conformation, the advancement splint includes an articulated frame having rigid and flexible elements, immersed in the thermoformable flexible material or molded around it. The frame's articulations (12, 13, 23) allow the splint to fit the curve of the dental arch and to adapt to irregularities in the teeth's position. The inventive splint is equivalent in terms of comfort and efficiency to a personalized splint made by an orthodontist or dental technician, but its cost is 6 to 10 times lower.

6 Claims, 7 Drawing Sheets

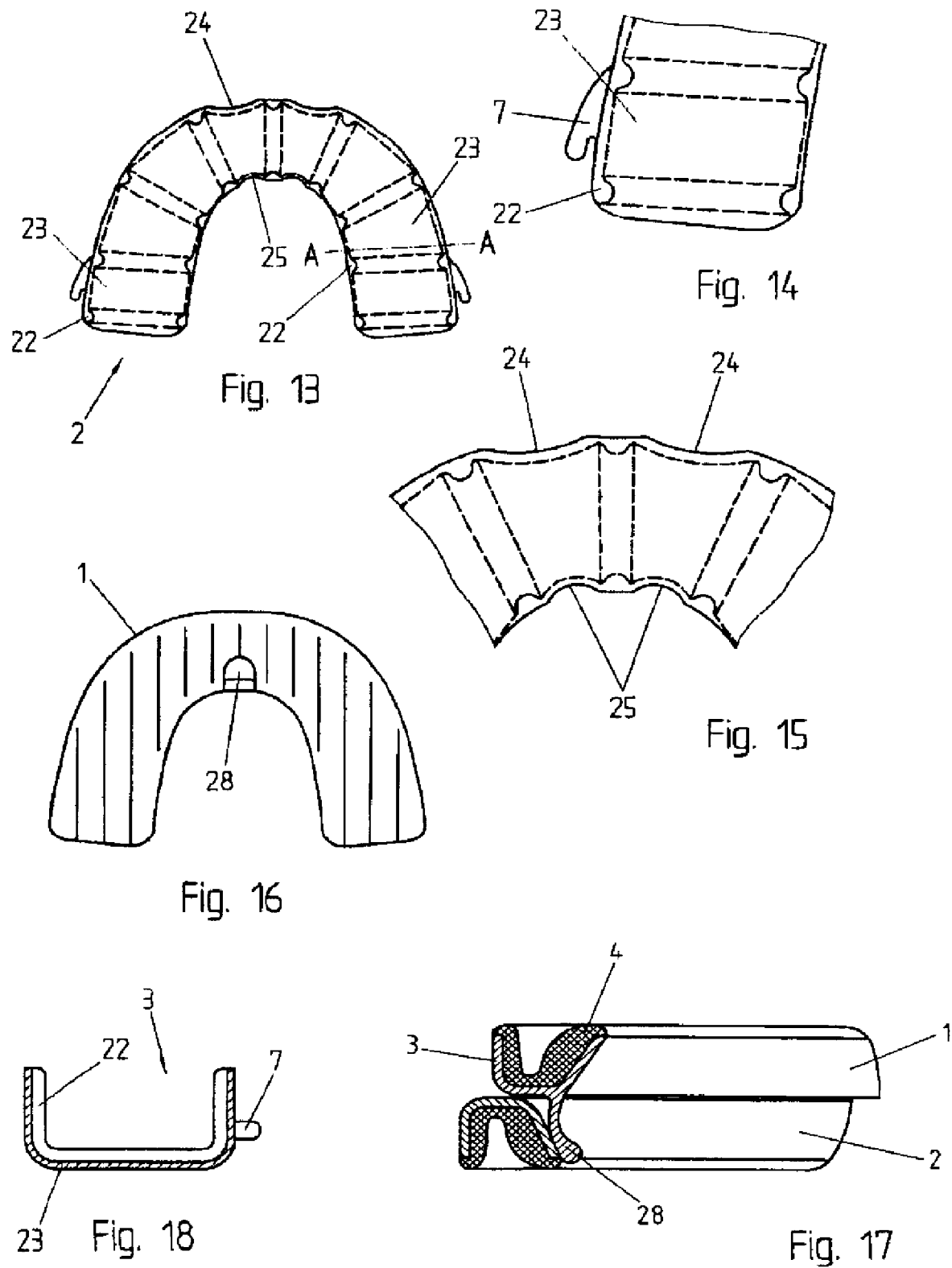

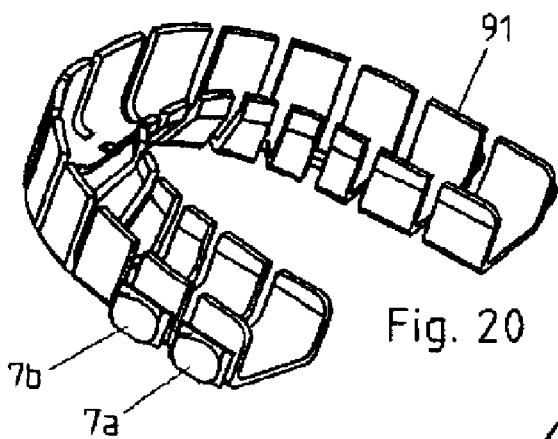
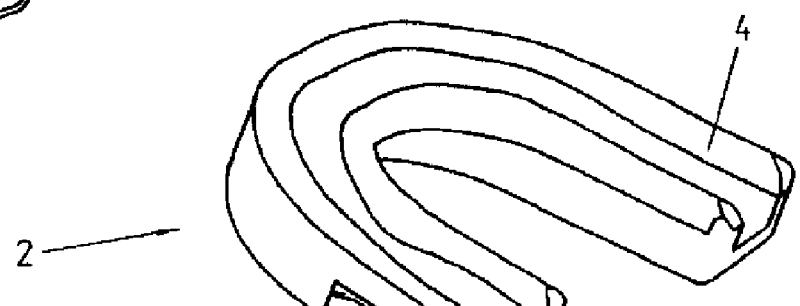
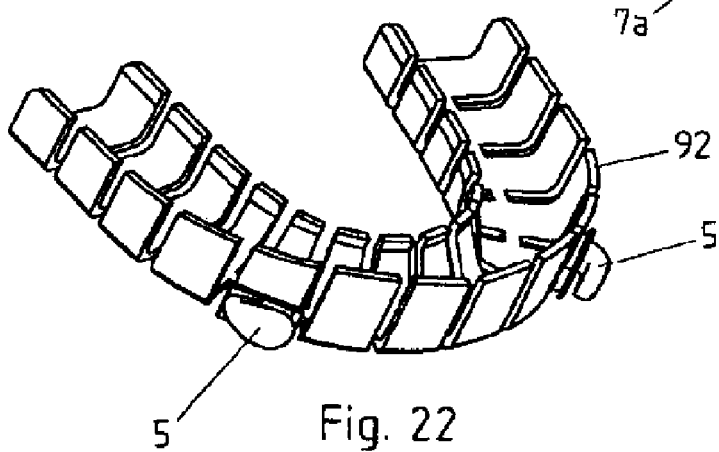
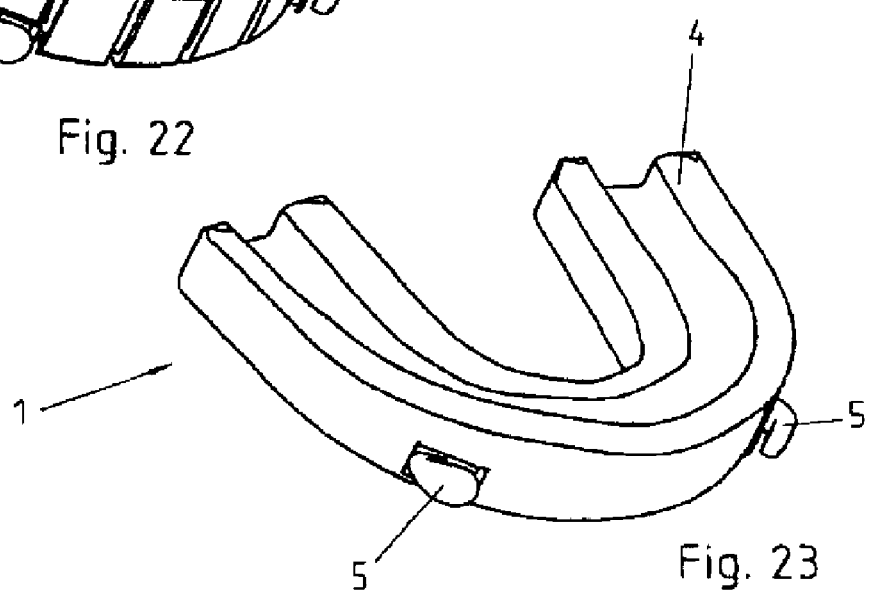

MANDIBULAR ADVANCEMENT SPLINT

REFERENCE DATA

This application is a divisional of application Ser. No. 11/562,344, filed Nov. 21, 2006, now abandoned which is a continuation of international patent application PCT/EP2005/052431, filed on May 27, 2005, claiming priority form European patent application EP04102543, filed on Jun. 4, 2004, all of which are incorporated herewith by reference.

TECHNICAL FIELD

The present invention relates to the field of mouth corrective appliances and notably to a mandibular advancement splint for treating snoring and night apnea.

RELATED ART

Snoring is a well-known acoustic expression whose anatomic and physiological causes are connected to a muscular hypotonia that appears during sleep. The mandible, normally held by the action of the muscles, in fact tends to move backwards during sleep, its movement causing the tongue to move towards the back of the mouth and thus the size of the upper air tract to diminish. The resulting turbulences of the respiratory flow, amplified by vibration and resonance phenomena of the soft palate (velum palatinum) and of the adjacent soft parts, are the origin of the snoring sound that can, in certain cases, reach an extremely high intensity.

Snoring is not limited to disturbing, even severely, the quality of sleep of the household and relatives of the afflicted person. Sometimes, especially with individuals suffering from macroglossia or from a small-size mouth cavity, or if the laxity of the tissues is high, the obstruction of the breathing canal can be serious or even complete, causing in fact the breathing to be interrupted or obstructive sleep apnea.

In this case, snoring is one aspect of a true pathology that also shows through the fragmentation of sleep provoking drowsiness during the day and lessened concentration abilities. Apnea causes hypoxia, bradycardia followed by tachycardia with risks of hypertension. This apnea is likely to trigger a nocturnal cardio-respiratory arrest.

It is known how to treat efficiently snoring and night apnea by wearing during the night a nasal mask blowing air under pressure into the pharynx. This solution however places an excessive constraint upon the wearer and requires individual calibrations for each patient, as well as polysomnographic efficiency controls. For these reasons, the application of this type of treatment is restricted to obstructive syndromes and is not justified for treating simple snoring. Prolonged use is likely for the treatment to cause nasal symptoms of the rhinitis type or skin sores that make it impossible to wear the mask.

It is also known how to treat snoring and sleep apnea by surgical resection of the soft palate, possibly completed with surgical maxillary advancement. This solution is however invasive and painful, and the resulting improvement is only transitory. Furthermore, it can involve changes of the mouth morphology that can disturb deglutition. This highly invasive operation is nowadays practically abandoned.

To fight snoring, mouth appliances that hook onto the upper and lower dental arches have been proposed, allowing the mandible to be advanced forward even in the absence of sufficient muscular tension. Patent application DE19844628 describes an example of such a mono-bloc device of the type immobilizing completely the mandible in advanced position. Having the mandible immobilized can prove discomforting for the wearer, notably in that it interferes with deglutition and can cause an algo-dysfunctional syndrome (ADS) of the temporo-mandibular joint (TMJ).

Patent EP0845962B describes a thermoformable articulated device combining supple and semi-rigid elements and allowing a certain freedom of movement of the mandible whilst advancing it forward. This device consists of two trays made of thermoformable material. In this manner, each patient can adapt the trays to his own conformation by heating in a water bath at a temperature sufficient for softening the thermoformable layer and then by molding them on the corresponding arch.

The conformation of the teeth and of the dental arches varies however considerably from one individual to another, either because the arches can be more or less wide for each individual, or because the teeth are not regularly positioned along each arch. The adaptability of known thermoformable devices is very limited and they cannot adapt to the full range of possible conformations.

When the mouth appliance cannot adapt perfectly to the individual dental conformation, the efficiency is reduced, the device is instable, there are excessive tensions on the dentition and the adaptation of the system is very uncomfortable. Furthermore, following the involuntary movements of clamping the mandible, high and concentrated mechanical efforts can occur on the trays' semi-rigid elements that can cause the device to rupture.

Another limitation of this type of appliances is that if it does not adapt perfectly to the dental conformation, it can, during use, exert lateral forces on the teeth that can be of high intensity. These lateral forces can, in time, lead to a displacement and destabilization of the teeth and to their definitive loss.

It is also known to make mandibular advancement splints specially manufactured to adapt to the wearer's dental conformation. In this case, each splint is made as a unique part according to the impression of the wearer's jaw bone and mandible, by conventional methods in the field of orthodontics. It will be easily conceived that the manufacturing cost of this kind of personalized apparatus is considerably higher than that of an adaptable splint manufactured in series.

Another limitation of the known mandibular devices, such as for example the devices described by EP0845962B, that allow a certain freedom of movement of the mandible, is that the latter can, following involuntary movements during sleep, abandon the forward advanced position. The device then completely loses its efficiency. In these cases, the freedom of movement in the backward direction paradoxically goes against the sought aim of mandibular advancement.

U.S. Pat. No. 5,829,441 describes a mandibular advancement splint having two flexible frames, allowing a deformation and an adaptation of the splint to different dental conformations, during a molding phase.

The wearer's position during sleep can also influence negatively the good functioning of the known mandibular devices. It is for example frequent for the mandible to abandon the forward advanced position when the head is positioned on the side.

It is also known that certain phases of sleep are characterized by a very high activity and muscular tonicity. Once these phases of agitated sleep over, the prior art devices are not always capable of automatically bringing the mandible in the advanced therapeutic position.

Another limitation of the known devices capable of being personalized is that they are based on a conventional mouth geometry where the teeth are parallel and arranged on two plane arches. These splints are not capable of adapting to most real dental conformations.

BRIEF SUMMARY OF THE INVENTION

One aim of the present invention is to propose a mandibular advancement splint that is without the disadvantages of the prior art.

Another aim of the present invention is to propose a mouth device against snoring that can adapt to a very large number of individual conformations without irreversible risks for the users dentition.

Another aim of the present invention is to propose a mouth device against snoring that is more comfortable than the known devices.

Yet another aim of the present invention is to propose a mandibular advancement splint that can adapt to the wearer's dental conformation having the comfort and efficiency equal to those of a personalized splint and a reduced production cost.

These aims are achieved by the device that is the object of the main claim.

BRIEF DESCRIPTION OF THE FIGURES

The invention will be better understood in the light of the following description, claims and figures in which notably:

FIGS. 13, 14 and 15 represent diagrammatically another embodiment of the invention;

FIGS. 16 and 17 show diagrammatically another embodiment of the invention comprising an elastic tongue;

FIG. 18 represents diagrammatically a cross section of the extrados of a splint according to the invention along the plane A-A of FIG. 13;

FIGS. 20, 21, 22 and 23 represent diagrammatically and in three dimensions the upper and lower elements of a device according to the invention as well as the respective flexible outer frames.

EXAMPLES OF EMBODIMENTS OF THE INVENTION

Figure 1:
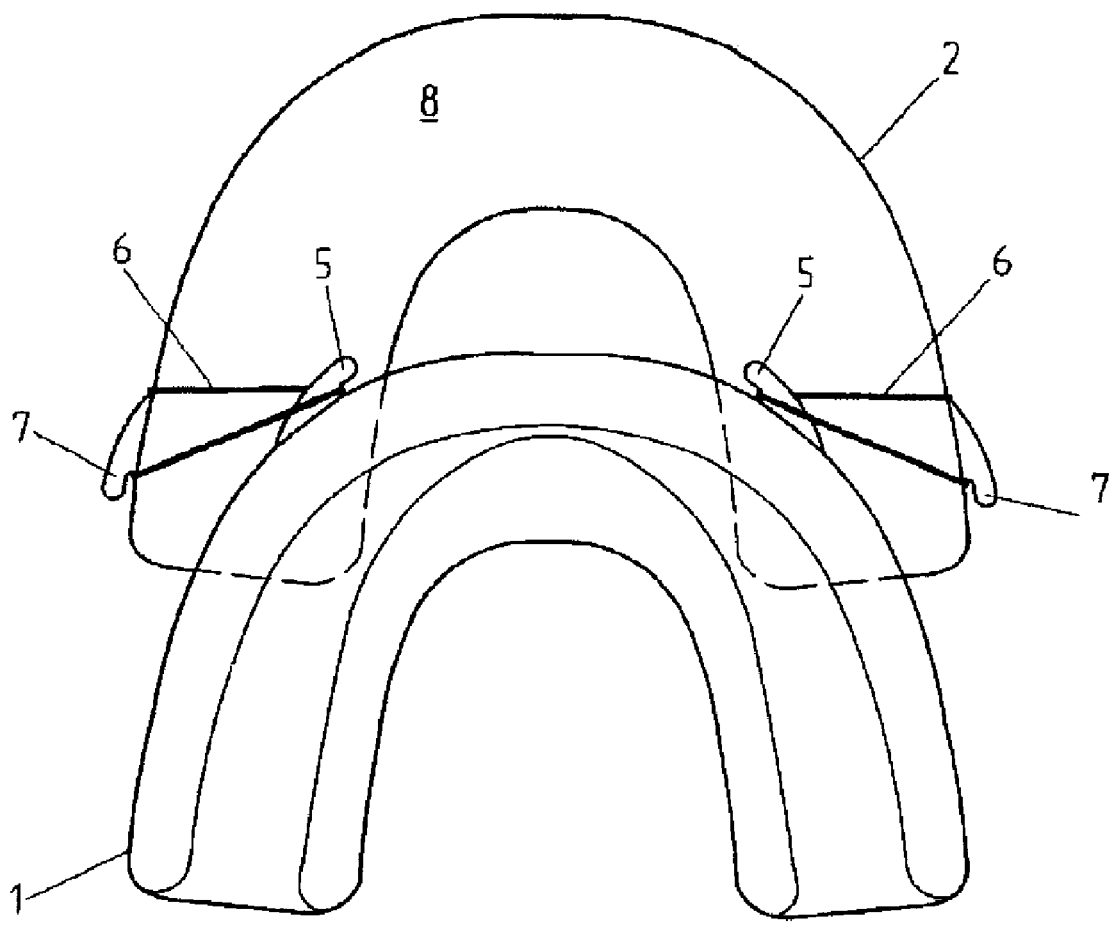
FIGS. 1 and 2 represent diagrammatically a mandibular advancement splint of known type.
Figure 2:
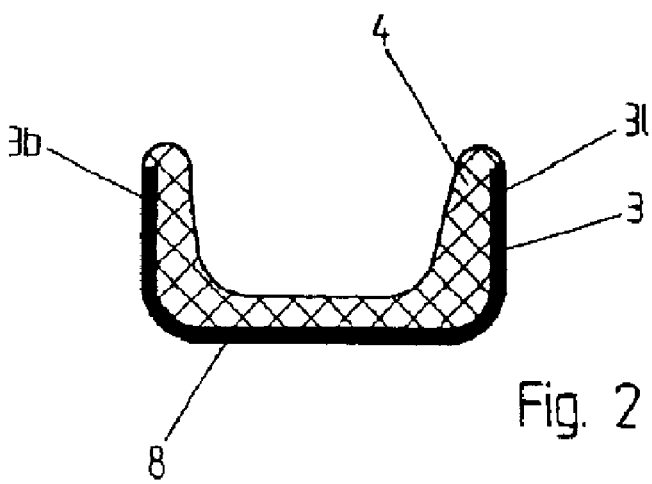

FIG. 1 represents an intrabuccal device against snoring of known type. It is composed of two trays 1, 2 designed to wrap the upper and lower dental arches. With reference to FIG. 2, the trays 1 and 2 have an extrados 3 essentially rigid on which a thermoformable intrados 4 is molded. The trays are connected to one another by the hooks 5 and 7 and the elastic loops 6 in order to exert on the mandible an advancement force while allowing a certain freedom of movement. The rigid extrados 4 of this device is incapable of following an irregular dentition. The device exerts a holding force against the teeth.

During use, the plane surfaces 8 of the two extrados find themselves in contact along the occlusion plane. The mandible's laterality and forward and backward movements thus include a sliding of these surfaces 8 one against the other.

In order to allow a personalized adaptation of this apparatus, each patient can adapt thetrays to his own conformation by molding the thermoformable intrados 4 on the corresponding arch, after having softened it by immersing it in a water bath at an appropriate temperature.

The device of FIG. 1 thus has a good conformability as long as all the teeth are positioned correspondingly to the flexible intrados. It is however frequent that the teeth do not follow exactly the curvature of the trays 1 and 2 and that one tooth finds itself corresponding to the extrados 3 when the impression is taken. In this situation, the splint cannot at all adapt to the arch.

Figure 4:
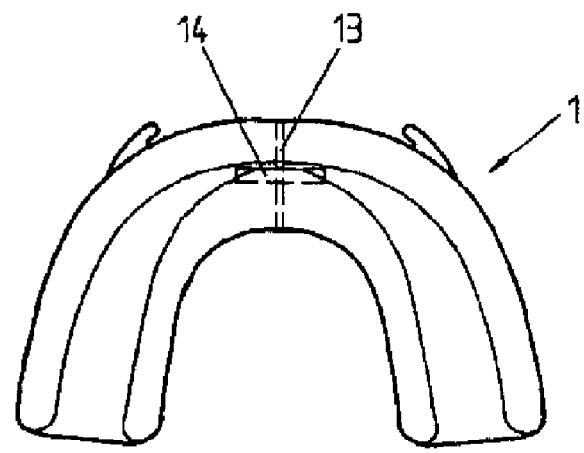
FIG. 4 represents diagrammatically a device having a flexible outer frame according to one aspect of the present invention.

FIG. 4 represents a tray of a device having an articulated frame according to the invention. In this device, the extrados includes at least one flexible joint so as to make an articulated frame to follow the patient's dental conformation, even in the case where the teeth are implanted irregularly.

In this simple embodiment, the inventive device is limited to a single central flexion point, situated corresponding to the midsagittal plane. The flexible joint is obtained by providing a slit 13 in the extrados 3. The considerably higher flexibility corresponding to the slit 13 allows the extrados 3 to be articulated. A flexible metallic or plastic element 14 can be inserted to connect the two right and left halves of the extrados 3. The inventive system can include one or several slits according to the sought degree of adaptability.

Figure 5:
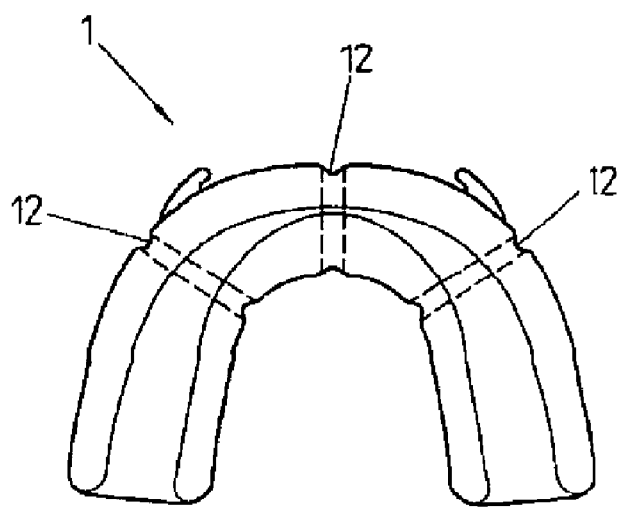
FIG. 5 represents diagrammatically a later variant embodiment of a device having a flexible outer frame according to one aspect of the present invention.

FIG. 5 represents, for the sake of simplification, the upper tray 1 only. The features that are characteristic of this embodiment of the invention can obviously also be advantageously incorporated into the lower tray 2.

The central slit 13 also allows the two trays to align correctly when the impression is taken. Optionally, the same function can be ensured by marks, preferably convex, engraved to this effect on both trays.

In the frame of the present invention, the elastic loops could be replaced by other equivalent means, for example by springs, pistons, flexible tongues provided in one or the other tray or by magnets.

Advantageously, the frame comprises a plurality of flexible joints to adapt to a wider range of dental conformations. FIG. 5 represents a tray of a device according to the invention provided with an extrados forming an articulated frame. The extrados 3 includes in this case three flexible joints 12 made by thinning the outer walls. Preferably, the extrados 3 will be made of a polymer capable of being formed by molding, having a good elasticity and being capable of bearing a great number of flexion cycles, for example of a thermoplastic elastomer.

The materials of which the extrados and the intrados are made are selected so as to provide a good adhesion between these two parts. A good chemical compatibility is thus important in order to achieve this result. The adhesion of the extrados with the intrados can be further improved by providing ribs or cavities in the extrados to provide a hooking surface during molding.

FIGS. 13, 14 and 15 show the flexible extrados of the lower tray 8 of a splint according to another embodiment of the invention.

In this embodiment, the flexible joints are made by thinning the inner walls of the extrados, which has the advantage of maintaining an outer surface that is perfectly smooth and of avoiding concave outer surfaces that are difficult to clean. The extrados includes in this variant embodiment alternating thin sections 23 and more rigid ribs 22. The thin sections 23 work essentially in flexion and in extension and allow the extrados to follow the general shape of the dental arch. The ribs 22, on the other hand, provide sufficient rigidity to ensure the splints lateral stability against the teeth and notably against the lingual and labial sides of the teeth.

It is important for the stability of the splint and for the dental health that the flanks 3*l* and 3*b* of the extrados 3 exert, through their rigidity, two opposed lateral forces on the lingual and labial sides of the teeth respectively. The inventive device, through its conformability, allows the symmetrical positioning of the two flanks 3*l* and 3*b* relative to the teeth and consequently anefficient holding without asymmetric forces, even if the teeth are positioned irregularly.

The conformability of the inventive trays allows the traction exerted by the elastic loops 6 to be spread correctly on a large number of teeth, typically 20 or more. It is thus possible in this manner to avoid collateral damages that could arise if the advancement force were to be applied on a limited number of teeth (for example deformation of the occlusion plane or displacement of teeth).

Advantageously, the zones more solicited in extension and in compression have thin curved walls 24, 25 to ensure greater elongations and compressions thanks to their flexibility. The curvature of the walls 24 and 25 could be towards the inside (concave) or towards the outside (convex) depending on the need.

FIG. 18 represents diagrammatically a cross section of the extrados 3 along the plane A-A of FIG. 13. One can see the thin section 23, traversed by the cross section plane A-A, and the rib 22 in the background.

Figure 6:
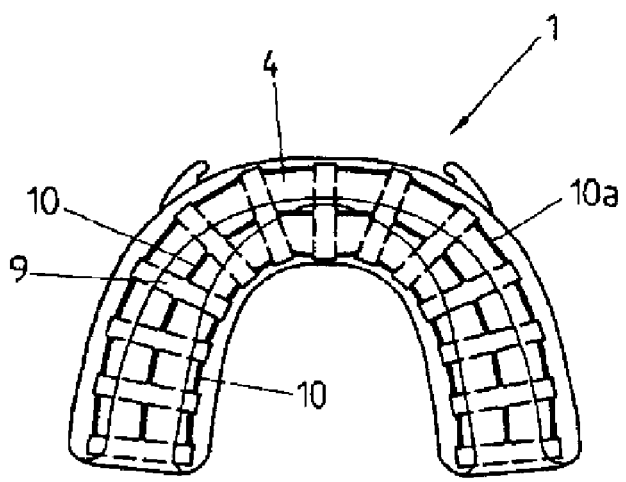
FIG. 6 represents diagrammatically a device having a flexible inner frame according to one aspect of the present invention.

Another embodiment of the invention will now be described with reference to FIG. 6. In this embodiment, a flexible and articulated frame is inserted inside a tray 4 of a flexible and thermoformable material. The flexible frame is composed of a succession of rigid U-shaped elements 9, open towards the dental arch, connected by thinner flexible elements 10 and 10*a*. Advantageously, the articulated frame is made of a single piece by molding a suitable material having a good elasticity and deformability and capable of bearing a very high number of flexion cycles at its thin section.

The flexible articulations 10 and 10*a* allow the frame to deform in the three dimensions of space, horizontally and vertically, as well as torsion movements. In this manner, the inventive device can fit perfectly the dental conformation in three dimensions, for example to adapt to the natural curvature of the dental occlusion surface or to a non parallel implantation of the teeth. (The designations "horizontal" and "vertical" refer here to the conventional orientation of the splint when it is worn by a wearer in upright position).

Figures 7, 8:
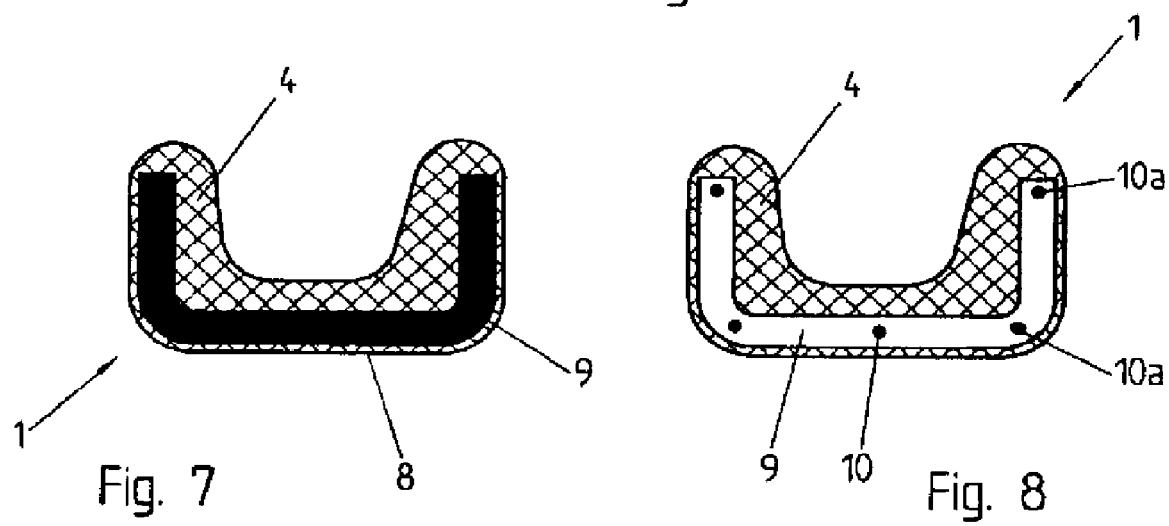
FIGS. 7 and 8 represent diagrammatically two sections of the device of FIG. 5.
Figure 9:
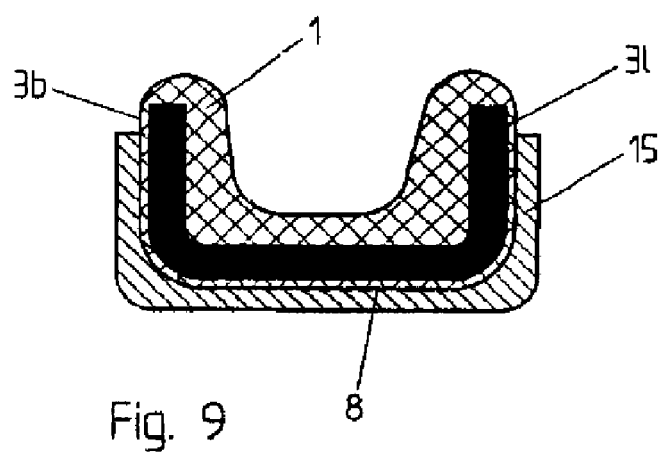
FIG. 9 represents diagrammatically one section of the device of FIG. 5 inserted into a cradle for taking impressions.

The mandibular advancement splint according to this embodiment of the invention has an outer surface that is completely flexible and thus provides superior comfort as compared with devices having rigid or semi-rigid outer surfaces. FIGS. 7 and 9 show two cross sections of the tray 4 of FIG. 6 in correspondence with the elements 9 and 10.

Another advantage of this embodiment of the invention is that the risks of the inner frame and the thermoformable part becoming unstuck are practically nil. The thermoformable tray 4 is molded around the flexible frame and completely envelops it.

Figure 19:
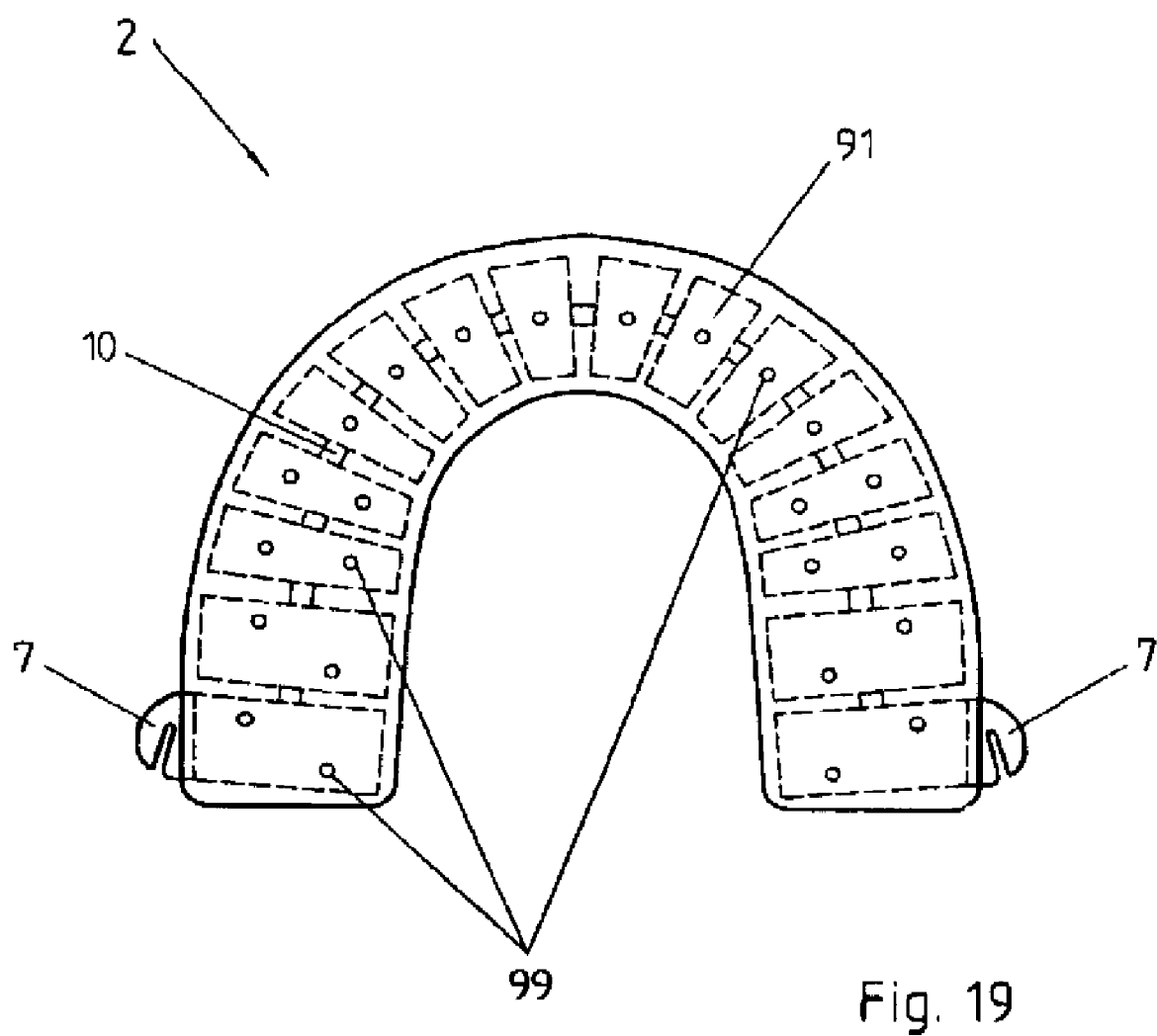
FIG. 19 represents diagrammatically a top view of the lower element of the inventive splint according to a preferred variant of the embodiment of FIG. 6.

FIG. 19 represents a top view of the lower element 2 of the inventive advancement splint made according to a preferred variant of the embodiment of the invention that has just been described. In this variant embodiment, the flexible articulated frame, visible in transparency in the figure, is composed of a greater number of U-shaped elements 91 relatively rigid, open towards the dental arch, connected by a relatively flexible ridge 10 or another flexible element that connects the elements 91. The articulated frame is made of a single piece by molding an appropriate material having a good elasticity and deformability, a minimal creep and capable of bearing a very high number of flexion cycles at its thin section, such for example as polyacetal of medical quality. Advantageously, the hooks 7 provided for fastening the elastic loop, are made integrally in the frame.

Preferably, the relatively rigid elements 91 have openings 99 to allow the thermoformable material to pass more easily when the tray 4 is molded around the frame. This characteristic could also be adopted in the other embodiments of the invention described, depending on the case.

FIG. 20 shows in three dimensions the lower inner frame of FIG. 19. In this variant embodiment, the frame bears two pairs of additional hooks 7*a*, 7*b* instead of a single pair. This arrangement makes it possible to modulate easily the advancement force exerted by the elastic bands (not represented) by simply selecting the fastening hook.

FIG. 21 shows, in three dimensions, the lower cradle 2, after the thermoformable tray 4 has been molded.

FIG. 22 represents, in the same way as FIG. 20, a frame for an upper cradle having a certain number of relatively rigid U-shaped elements 92 open towards the dental arch, connected by flexible ridges. FIG. 23 shows the upper cradle 1 after the thermoformable material 4 has been molded.

This embodiment of the invention has the advantage that the cradles can deform, when the impression is made, in all directions in space. The inventive frame can thus not only open and close in the horizontal plane to adapt to a more or less open mandible or jaw, but it can also curve vertically to fit the curvature of the occlusion surface and twist according to the direction in which the teeth are implanted.

Thanks to this characteristic, the inventive advancement splint can adapt, in three dimensions, to any dental conformation of the wearer.

FIG. 9 illustrates an interface element 15 that intervenes when the impression is taken for the inventive device. The aim of this device is to prevent, when the impression is made, the two flanks 3*l* and 3*b* from moving apart, which would have the effect of reducing the pressure on the lingual and labial sides of the teeth and, consequently, the stability of the splint. To this effect, the trays are inserted, for making the impression only, in two interface elements in the shape of disposable flexible cradles 15 that prevent the surface 8 from deforming and the flanks 3*l* and 3*b* from moving apart.

It is also important that the two trays that make up the advancement splint have two sliding planes 8 perfectly adapted to one another. Using interface elements 15 makes it possible to prevent any deformation of said planes when the impression is made.

A symmetric cradle is provided for the lower tray. Once the cradles 1 and 2 have been molded on the arches, the interface elements 15 can be removed after the thermoformable elements 4 have cooled.

These interface elements 15 can also be advantageously used in other embodiments presented, whilst remaining within the frame of the present invention.

Figure 3:
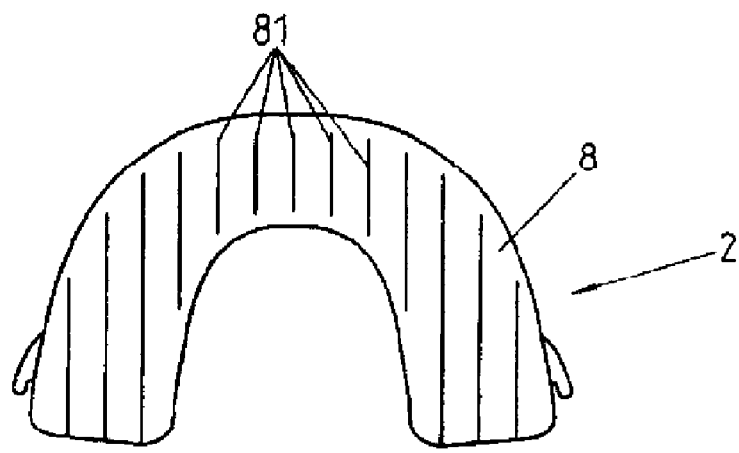
FIG. 3 represents diagrammatically a device having convex sliding striations and allowing an air flow to pass according to one aspect of the invention.

Optionally, the sliding plane 8 of at least one of the trays 1 and 2 has a plurality of parallel convex striations 81 or other types of relief to improve sliding as represented in FIG. 3.

Figure 11:
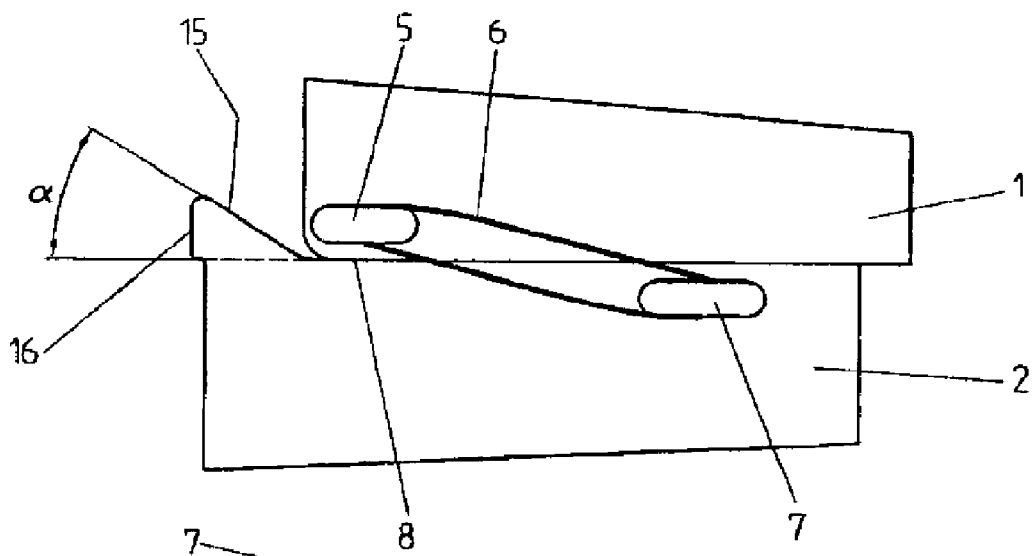
FIGS. 11 and 12 represent diagrammatically another embodiment of the invention comprising a surface inclined relative to the main sliding plane.
Figure 12:
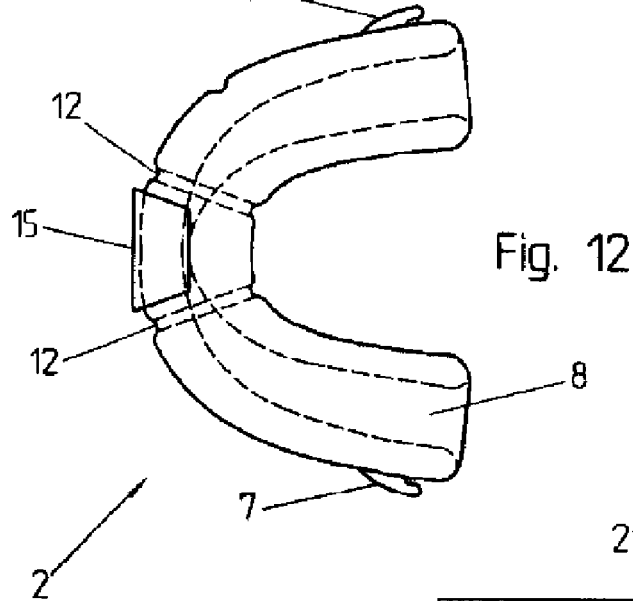

With reference to FIGS. 11 and 12, the lower tray 2 has, at the front extremity, a protrusion 16 with an inclined plane 15, oriented in the direction of increasing the advancement force during a backward movement of the mandible, thus contributing to keeping the advanced position. It has been seen that, during sleep, the mandible sometimes involuntarily moves backwards. These movements are physiological during sleep and deglutition and it would not be conceivable to lock the mandible in a static advanced position. This embodiment thus makes it easier for the mandible to return to the advanced position after these movements.

Figure 10:
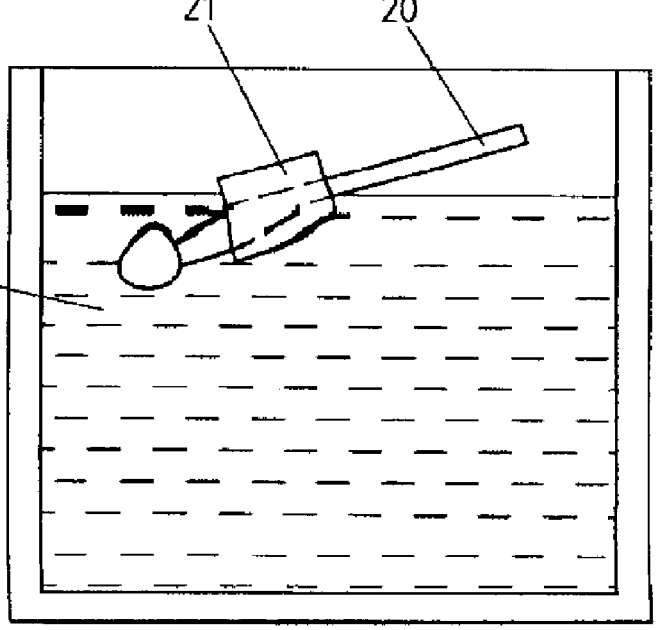
FIG. 10 represents diagrammatically a calibrated temperature indicator used in the method for taking impressions according to the invention.

FIG. 10 represents a thermometer for measuring the temperature of a hot water bath designed to facilitate the shaping of the inventive devices.

Making the impression includes previously immersing the trays in a cold water bath that is then brought to a temperature of about 75° degree. C.

Traditional glass thermometers have the tendency of moving to the bottom of the bath 100 and will thus record a much higher temperature than the prescribed temperature of the bath. Furthermore, devices that are too light, for example those using liquid crystals, are easily transported by the movements of simmering liquid and reading them is not easy.

The thermometer 20 has an asymmetric floater 21 that determines a hydrostatic equilibrium position inclined relatively to the vertical axis of the thermometer 20. This arrangement makes it easier to read the temperature. The thermometer's equilibrium position is preferably chosen so that the thermometer's sensing bulb is, in the water, at the same height as the floating trays 1 and 2.

With reference to FIGS. 16 and 17, another embodiment of the present invention provides a flexible elastic tongue 28 made integrally in the supper tray 1 during molding. Other positions, for example further back, are however possible and comprised within the present invention.

The tongue 28 rests against the lower tray 2 when the advancement is in its normal use position and exerts a advancement force on the lower tray and the postero-anterior direction, thus positioning the mandible in the sought advanced position to prevent snoring, whilst allowing sufficient freedom for involuntary movements during sleep.

The invention claimed is:

1. A mandibular advancement splint adaptable to different dental conformations, the mandibular advancement splint comprising:
   a first tray for enveloping an upper dental arch of a wearer's mouth cavity;
   a second tray for enveloping a lower dental arch of the wearer's mouth cavity;
   an advancement means connecting said first and second trays that is capable of exerting an advancement force onto said second tray in the postero-anterior direction,
   wherein at least one of said first and second trays includes an articulated frame, said articulated frame having
      a plurality of rigid U-shaped elements configured to exert a holding force against labial and lingual sides of a wearer's teeth, and
      one or more flexible elements configured to connect said plurality of U-shaped elements and to allow said frame to articulate and/or deform along three dimensions to adapt to a wearer's dental conformation, and
   wherein said plurality of U-shaped elements open toward the wearer's teeth.

2. The mandibular advancement splint of claim 1, having elements of thermoformable plastic material in said first and second trays to adapt to the wearer's dental conformation.

3. The mandibular advancement splint of claim 2, wherein said frame is inside said elements of thermoformable plastic material.

4. The mandibular advancement splint of claim 1, wherein said advancement means include elastic loops.

5. The madibular advancement splint of claim 1, wherein said flexible elements comprise slots located between said rigid elements.

6. The madibular advancement splint of claim 1, wherein a lateral dimension of said flexible element is less than a corresponding lateral dimension of said U-shaped prehension elements.

* * * * *